United States Patent [19]

Nakamoto

[11] Patent Number: 5,082,786
[45] Date of Patent: Jan. 21, 1992

[54] GLUCOSE SENSOR WITH GEL-IMMOBILIZED GLUCOSE OXIDASE AND GLUCONOLACTONASE

[75] Inventor: Shinya Nakamoto, Tokyo, Japan
[73] Assignee: NEC Corporation, Tokyo, Japan
[21] Appl. No.: 276,663
[22] Filed: Nov. 28, 1988
[51] Int. Cl.$^5$ .......................... C12M 1/40; C12Q 1/54
[52] U.S. Cl. ...................... 435/288; 435/14; 435/177; 435/817
[58] Field of Search ............... 435/288, 18, 25, 817, 435/175, 177, 14

[56] References Cited

U.S. PATENT DOCUMENTS

| 4,066,512 | 1/1978 | Lai et al. | 195/127 |
| 4,224,125 | 9/1980 | Nakamura et al. | 435/817 |
| 4,601,981 | 7/1986 | Vieth et al. | 435/94 |

OTHER PUBLICATIONS

Pocker et al, "Hydrolysis of D-Glucono-δ-lactone", *Journal of the American Chemical Society*, vol. 95, No. 1, Jan. 10, 1973, pp. 113–119.
Henozato et al, "Multi-Enzyme Electrode Using Hydrogen-Ion-Sensitive Field-Effect Transistors", *IEEE Transactions on Electron Devices*, vol. ED33, No. 1, Jan. 1988, pp. 47–51.
Hanazote et al, "Glucose Sensitive Field-Effect Transistor with a Membrane Containing Co-Immobilized Gluconolactonase and Glucose Oxidase", 9-15-88, pp. 47–59.
The 1984 Enzyme Nomenclature Book, 1984, pp. 50, 51 and 73–74.
Dixon and Webb, *Enzymes*, 2nd Ed., Academic Press Inc., 1964, pp. 16, 17, 734.
"Glucoamylase and Glucose Oxidase Preparations and Their Combined Application for Conversion of Mattose to Gluconic Acid", *Biotechnology and Bioengineering*, vol. 19 (1977), pp. 185–198.
"Purification and Partial Characterization of Beef Liver Gluconolactonase", *Archives of Biochemistry and Biophysics*, vol. 192, No. 2, Feb. 1979, pp. 482–488.
"pH-Based Enzyme Potentiometric Sensors", *Anal. Chem.*, vol. 57, pp. 1920–1923.
"pH-Based Enzyme Potentiometric Sensors", *Anal. Chem.*, vol. 57, pp. 1924–1925.
"Immobilized Enzyme Electrode Probes", *Solid Phase Biochemistry*, published by John Wiley & Sons, New York (1983), pp. 479–505.

Primary Examiner—David L. Lacey
Assistant Examiner—Janelle D. Waack
Attorney, Agent, or Firm—Burns, Doane, Swecker & Mathis

[57] ABSTRACT

A glucose sensor in which a gel is in contact with a pH sensing element. The gel contains immobilized glucose oxidase and gluconolactonase (EC 3.1.1.17). Gluconolactonase is present in an amount effective to accelerate the hydrolysis of D-glucono-δ-lactone.

5 Claims, 2 Drawing Sheets

GLUCOSE SENSOR WITH GEL-IMMOBILIZED GLUCOSE OXIDASE AND GLUCONOLACTONASE

BACKGROUND OF THE INVENTION

1. Field of the Invention

The present invention relates to a glucose sensor, more particularly a glucose sensor comprising a gel in which glucose oxidase is immobilized and a pH-sensing element.

2. Description of the Related Art

A variety of types of glucose sensors have been proposed to determine the concentration of glucose in a solution. The conventional techniques of immobilized enzyme electrode probes are shown in "Solid Phase Biochemistry" published by John Wiley & Sons, New York, 1983, page 479 to 505. Although many models of glucose sensors have been proposed, their common principle for measuring the concentration of glucose is based on the oxidation reaction of glucose which is catalyzed by glucose oxidase (abbreviated as GOD hereinafter).

In the glucose sensor, oxygen ($O_2$) consumed by the oxidation reaction of glucose, and hydrogen peroxide ($H_2O_2$) and gluconic acid which are produced by the oxidation reaction of glucose are sensed or measured by means of electrochemical elements to determine the concentration of glucose. The electrochemical elements may consist of a pH glass electrode or a hydrogen-ion-sensitive field effect transistor (abbreviated as pH-ISFET, hereinafter) which detects pH-change or pH-variation caused by the production of gluconic acid.

An example of the pH glass electrode is disclosed in "Biochimica et Biophysica Acta," Nilsson et al., 1973, vol 320, page 529, while a variety of models of the glucose sensors using the pH-ISFET have been proposed recently, for example "IEEE Transactions on Electron Devices," 1986, vol. ED-33, No. 1, page 47. In these conventional glucose sensors, a gel containing a GOD, which is available on the market, is held or deposited on a pH-sensing region of the pH-ISFET.

In the pH-change sensing type of enzymatic glucose probes above-mentioned, protons dissociated from gluconic acid produced by hydrolysis of D-glucono-δ-lactone, which is a direct product of the oxidation reaction of glucose are detected.

Gluconic acid possesses a dissociation constant (pKa) lower than 4 and hence is dissociated almost completely into a proton and a conjugate base at a pH range higher than 6. On the other hand, the D-glucono-δ-lactone which is produced by the oxidation reaction of glucose is almost completely hydrolyzed at a pH range higher than 5, since equilibrium in the hydrolysis reaction of the D-glucono-δ-lactone at the pH range higher than 5 is shifted excessively to the side of gluconic acid formation.

Therefore, if the pH is higher than 6, the D-glucono-δ-lactone which is a direct product of the oxidation reaction of glucose is hydrolyzed almost completely into gluconic acid which in turn is dissociated almost completely into a proton and a conjugate base, so that it can be considered that there is a relationship of 1:1 between the amount of glucose which is consumed by the oxidation reaction of glucose and the amount of protons which are detected. In the pH-change sensing type of enzymatic glucose probes, since the pH-change created on the pH sensing region is detected through the above-mentioned reaction scheme it is preferable that the hydrolysis reaction of D-glucono-δ-lactone proceed as fast as possible and also that the consumption rate of glucose and the formation rate of gluconic acid are balanced.

However, the rate constant of reaction in the hydrolysis of D-glucono-δ-lactone is in the order of $10^{-3}$ sec$^{-1}$ (Y. Pocker et al., "Journal of American Chemical Society," 1973, vol 95, page 113) in the case of spontaneous hydrolysis reaction. This means that it takes more than 10 minutes to hydrolyze half of the amount of D-glucono-δ-lactone at ambient temperature and at neutral pH.

Therefore, in the pH-change sensing type of enzymatic glucose probes in which the oxidation reaction of glucose proceeds in the gel containing the reference substance GOD, if the velocity of the hydrolysis of D-glucono-δ-lactone is slow, the greater portion of the D-glucono-δ-lactone which is produced by the oxidation reaction of glucose disappears or is lost out of the gel before it is converted to gluconic acid, so that the portion which disappears or is lost does not contribute to pH-change on the pH-sensing region of the glass pH-electrode or of the pH-ISFET.

In fact, it was confirmed by the present inventor that no response to glucose was observed in a case where GOD of high purity (GI obtained from ORIENTAL KOBO Co., Ltd. and Bühlinger Mannheim) was used in an pH-ISFET glucose sensor which was constructed according to a method disclosed in Japanese Patent Application No. 59-209165 (Laid-Open No. 61-88135, published May 6, 1986), even if the buffer capacity of a solution to be measured was lowered to the order of 0.002. This means that it is necessary to accelerate hydrolysis of D-glucono-δ-lactone in the pH-change sensing type of enzymatic glucose probes.

In the course of a study which was conducted to solve such problems, it was found that some of the GOD available on the market exhibited gluconolactonase (EC 3.1.1.17) activity which accelerates the hydrolysis of D-glucono-δ-lactone and that the out-put of the pH-ISFET glucose sensors containing such gluconolactonase were as high as the same level of those that had been reported.

Although it was already reported in "Biotechnology and Bioengineering," 1977, Vol. 19, page 185, that gluconolactonase is contained in commercially available GOD, this paper relates to reactions for preparing gluconic acid from maltose but mentions nothing about utilization of gluconolactonase in the pH-change sensing type of enzymatic glucose sensors.

The present inventor found that the gluconolactonase can be used as an accelerator of the hydrolysis of D-glucono-δ-lactone and completed present invention.

Therefore, an object of the present invention is to overcome the problem of the prior arts above, mentioned by accelerating the hydrolysis of D-glucono-δ-lactone and to provide an improved glucose sensor whose out-put signals are sufficiently high and hence is applicable for practical uses even at low concentrations of glucose.

SUMMARY OF THE INVENTION

The present invention provides a glucose sensor comprising a gel in which glucose oxidase is immobilized and a pH sensing element, characterized in that the gel contains gluconolactonase (EC 3.1.1.17).

The proportion of the gluconolactonase to be added to the glucose oxidase-containing gel is such an amount as is necessary and satisfactory to hydrolyze immediately the D-glucono-δ-lactone which is produced by the oxidation reaction of glucose. Good results are achieved when 500 units of gluconolactonase exist in 1 cm$^3$ of the gel in which the enzyme is immobilized in order to keep the consumption rate of glucose caused by the oxidation reaction of glucose in equilibrium with the formation rate of gluconic acid. The amount of the enzyme is determined by the method of SHIMIZU ("Analysis Method of Enzymes," Khodansha, 1977, page 22), assuming that Michaelis' constant is approximately 10 mM (G. D. Bailey, "Archives of Biochemistry and Biophysics," Vol 192, No. 2, 1979, page 482). In actual operation, more than 500 units of enzyme are preferably added to the gel in order to compensate deactivation of the enzyme during the preparation stage of the enzyme as well as physical hindrance cause by the matrix of the gel.

As mentioned above, there is a possibility that the commercially available GOD may contain gluconolactonase as a contaminant. However, the proportion of the gluconolactonase in the GOD is too small to guarantee the above-mentioned active amount in the gel, therefore the amount of GOD itself must be adjusted to assure the above-mentioned activity. It often happens that too much of the GOD, which make preparation of the gel difficult, is required when the amount of gluconolactonase is too small.

Moreover, the out-put of the pH-change sensing type of enzymatic glucose probes which are constructed by the commercially available GOD available on the market such as disclosed in the document mentioned above, is relatively weaker than the other type of enzyme sensors such as penicillin sensors (S. D. Caras et al., "Anal. Chem.," 1985, vol. 57, page 1920) or urea sensors (IEEE Transaction on Electron Devices, 1986, vol. ED-33, No. 1, page 47).

Therefore, the amount of gluconolactonase contained as a contaminant in the GOD available on the market is insufficient to obtain practical activity. This means that even if the GOD available on the market contains gluconolactonase as a contaminant, it is still necessary to add a predetermined amount of gluconolactonase freshly.

The pH-sensors used in the present invention may be a pH-ISFET, a glass sensor or the like.

According to the present invention, gluconolactonase, which catalyzes the hydrolysis reaction of D-glucono-δ-lactone, is added to the GOD-containing gel in order to promote the hydrolysis of D-glucono-δ-lactone and to balance the rate of glucose consumed in the gel with the formation rate of gluconic acid which is produced by the hydrolysis of D-glucono-δ-lactone, so that the sensitivity or out-put of the pH-sensor is improved.

As described above, the glucose sensor according to the present invention has the enzyme immobilized gel containing gluconolactonase, so that an increase sensor out-put is obtained even for lower concentrations of glucose and hence the lower limit of detection in the pH-sensing type glucose sensors is expanded.

DESCRIPTION OF THE PREFERRED EMBODIMENT

Now, the present invention will be described in more detail with reference to examples.

Gluconolactonase used in the examples was extracted from beef liver and purified by the method of Bailey et al. described in "Archives of Biochemistry and Biophysics," vol. 192, No. 2, page 482, 1979. The specific activity of the purified gluconolactonase was 1,100 units/mg at 25° C. and pH=7.5 (one unit of activity is defined as the amount of D-glucono-δ-lactone required to hydrolyze 1μmol of gluconolactonase for one minute).

GOD used was obtained from ORIENTAL KOBO Co., Ltd.

EXAMPLE 1

Preparation of the gel

A layer of enzyme immobilized gel was formed on the gate region of a pH-ISFET by a lift-off method described in the Japanese Patent Application No. 59-209165 (Laid-Open No. 61-88135, published May 6, 1986) Table 1 shows the composition of a protein solution spin-coated.

TABLE 1

| Solution | Part by volume |
| --- | --- |
| 30 wt % aqueous solution of bovine serum albumin | 3 |
| 30 wt % aqueous solution of GOD | 3 |
| 10 wt % aqueous solution of gluconolactonase[1] | 2 |
| 5 wt % aqueous solution of glutaraldehyde | 2 |

Note:
[1] gluconolactonase is dissolved in an aqueous solution of 10 mM of $MgCl_2$.

As a control, a comparative example of an enzyme immobilized gel was prepared by the same method as above except that the solution of gluconolactonase is replaced by a protein solution containing 10 mM of $MgCl_2$.

Each layer of the enzyme immobilized gels prepared has a thickness of 1 μm.

EXAMPLE 2

Preparation of the gel

An enzyme immobilized gel was prepared on the gate region of a pH-ISFET by a method described in "Sensors and Actuators," vol. 7, page 233. Table 2 shows the composition of a protein solution prepared.

TABLE 2

| Solution | Part by volume |
| --- | --- |
| 10 wt % aqueous solution of 2-hydroxy methylmethacrylic acid | 1 |
| 20 wt % aqueous solution of GOD | 1 |
| 10 wt % aqueous solution of gluconolactonase[1] | 1 |
| 1 wt % aqueous solution of riboflavin | 1 |
| 1 wt % aqueous solution of potassium persulfate | 1 |

Note:
[1] gluconolactonase is dissolved in an aqueous solution of 10 mM of $MgCl_2$.

A mixture having the composition was dropped on the gate wells on a pH-ISFET. Then, the above described is exposed to ultraviolet radiation to polymerize 2-hydroxy methylmethacrylic acid to obtain an enzyme immobilized gel.

As a control, a comparative example of an enzyme immobilized gel was prepared by the same method as above except that the solution of gluconolactonase is replaced by an aqueous solution containing 10 mM of $MgCl_2$.

Each layer of the enzyme immobilized gels prepared has a thickness of 200 μm.

EVALUATION OF RESPONSE PROPERTIES

Figure 1:
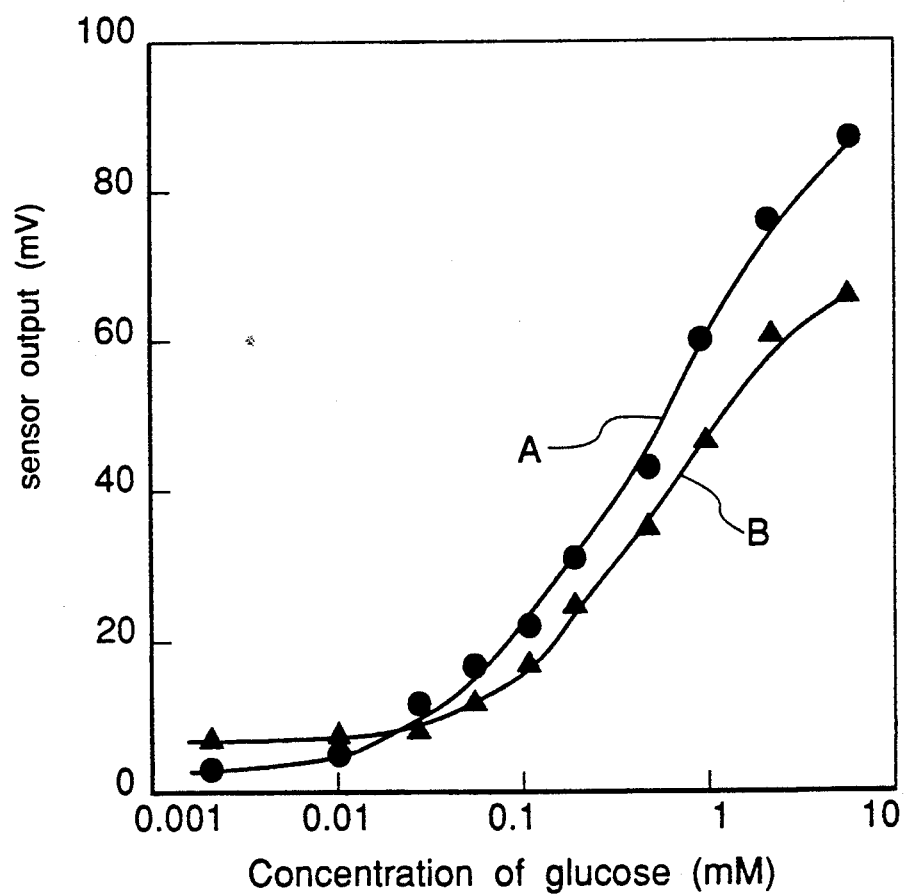
FIG. 1 shows the relationship between the concentration of glucose and the sensor out-put in the glucose sensors according to the present invention.
Figure 2:
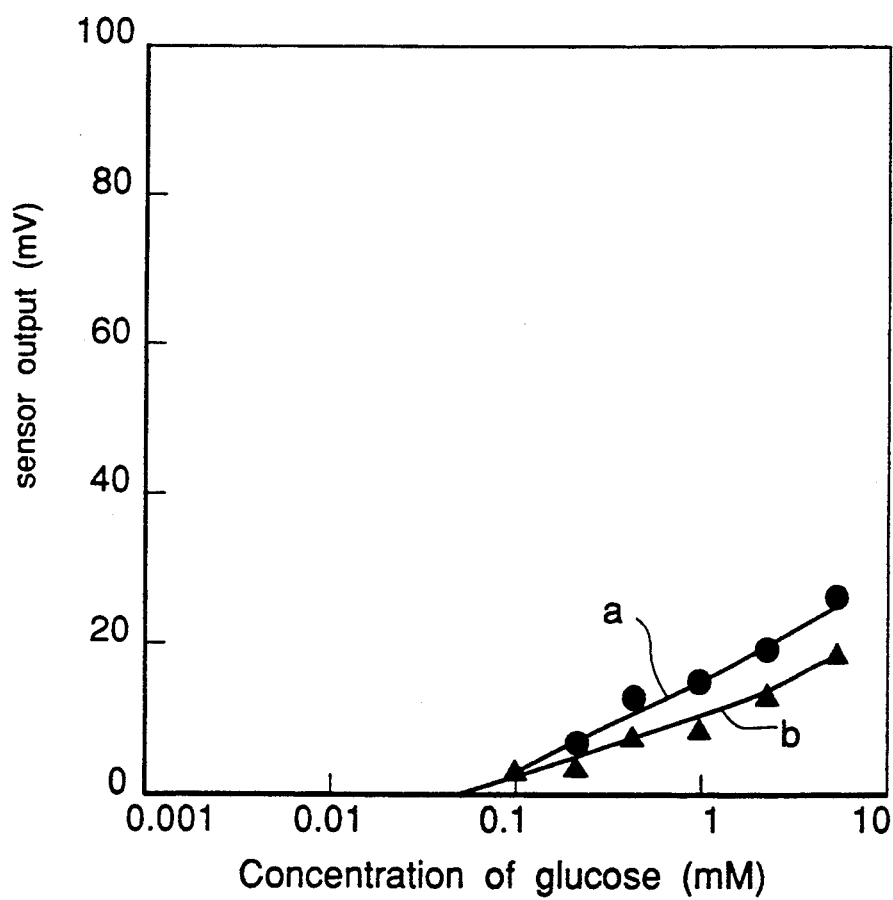
FIG. 2 shows the relationship between the concentration of glucose and the sensor out-put in the glucose sensors according to the prior art.

The results of the response properties of the glucose sensors prepared are shown in FIG. 1 and FIG. 2.

The response of the glucose sensor is determined in a 20 mM (N-2-hydroxyethylpiperazine-N'-2-ethanesulfonic acid-NaOH) buffer solution (pH=7.5) at 25° C.

Curve "A" in FIG. 1 is a response curve of the glucose sensor prepared by Example 1 according to the present invention, while curve "B" in FIG. 1 is a response curve of the glucose sensor prepared by Example 2 according to the present invention.

FIG. 2 shows response curves of the glucose sensors prepared by the comparative examples containing no gluconolactonase. Curve "a" in FIG. 2 corresponds to the curve "A" in FIG. 1, while curve "b" in FIG. 2 corresponds to the curve "B" in FIG. 1.

From the comparison of FIG. 1 and FIG. 2, it was revealed that the out-put of glucose sensor having the gluconolactonase-containing GOD immobilized gel according to the present invention increases remarkably from 0.01 mM of the concentration of glucose, so that the glucose sensors according to the present invention can be used in a wide range of concentrations of glucose from 0.01 to 10 mM. To the contrary, the conventional glucose sensors having the GOD immobilized gel containing no gluconolactonase shown in FIG. 2 do not produce satisfactory sensor out-put over about 0.1 mM of the concentration of glucose.

I claim:

1. A glucose sensor comprising (1) a gel in which glucose oxidase is immobilized and (2) a pH sensing element in sensing contact with said gel wherein said gel contains gluconolactonase (EC 3.1.1.17) in an amount effective to accelerate the hydrolysis of D-glucono-δ-lactone.

2. A glucose sensor as set forth in claim 1 wherein the pH sensing element is a pH-ISFET.

3. A glucose sensor as set forth in claim 1 wherein the pH sensing element is a pH glass electrode.

4. A glucose sensor as set forth in claim 1 wherein the gel contains crosslinkable polymer.

5. A glucose sensor as set forth in claim 1 wherein said gluconolactonase amount in said gel is in an amount of more than 500 units per one cubic centimeter up to a limit in which concentration is still effective to accelerate the hydrolysis of D-glucono-δ-lactone.

* * * * *

UNITED STATES PATENT AND TRADEMARK OFFICE
CERTIFICATE OF CORRECTION

PATENT NO. : 5,082,786

DATED : January 21, 1992

INVENTOR(S) : Shinya NAKAMOTO

It is certified that error appears in the above-identified patent and that said Letters Patent is hereby corrected as shown below:

Title page, item

[30]        Foreign Application Priority Data

Nov. 26, 1987 [JP]    Japan ............Showa 62-296011

Signed and Sealed this

Twentieth Day of April, 1993

*Attest:*

MICHAEL K. KIRK

*Attesting Officer*      *Acting Commissioner of Patents and Trademarks*